United States Patent [19]

Saupe et al.

[11] Patent Number: 4,696,645
[45] Date of Patent: Sep. 29, 1987

[54] APPARATUS FOR REMOVING PLAQUE AND STAINS FROM THE SURFACES OF TEETH

[75] Inventors: Martin Saupe, Offenbach; Hans Dauernheim, Dreieich; Maximillian Markl, Königstein, all of Fed. Rep. of Germany

[73] Assignee: Emda Fabrik Elektro-Medizinischer und Dentaler Apparate Georg Hartmann GmbH & Co. KG, Frankfurt am Main, Fed. Rep. of Germany

[21] Appl. No.: 790,731

[22] Filed: Oct. 24, 1985

[30] Foreign Application Priority Data

Oct. 30, 1984 [DE] Fed. Rep. of Germany ....... 3439584

[51] Int. Cl.4 ............................................. A61C 3/00
[52] U.S. Cl. ..................................... 433/125; 51/439; 433/88
[58] Field of Search .................. 433/125, 126, 82, 88, 433/80; 57/439, 317

[56] References Cited

U.S. PATENT DOCUMENTS 4,097,995 7/1978 Danne et al. ...................... 433/125
4,462,803 7/1984 Landgraf et al. .................. 433/125

Primary Examiner—Robert Peshock
Attorney, Agent, or Firm—Peter K. Kontler

[57] ABSTRACT

Apparatus for removing plaque and/or stains from the surfaces of teeth has an elongated handle which contains a removable cartridge for a supply of flowable solid material and whose nozzle defines a mixing chamber receiving solid material from the cartridge and further receiving compressed air from an adapter which is also connectable to a dentist's drill. The adapter further supplies a stream of water which is discharged by the nozzle through a first orifice. A second orifice of the nozzle communicates with and receives from the mixing chamber a mixture of compressed air and solid material.

26 Claims, 11 Drawing Figures

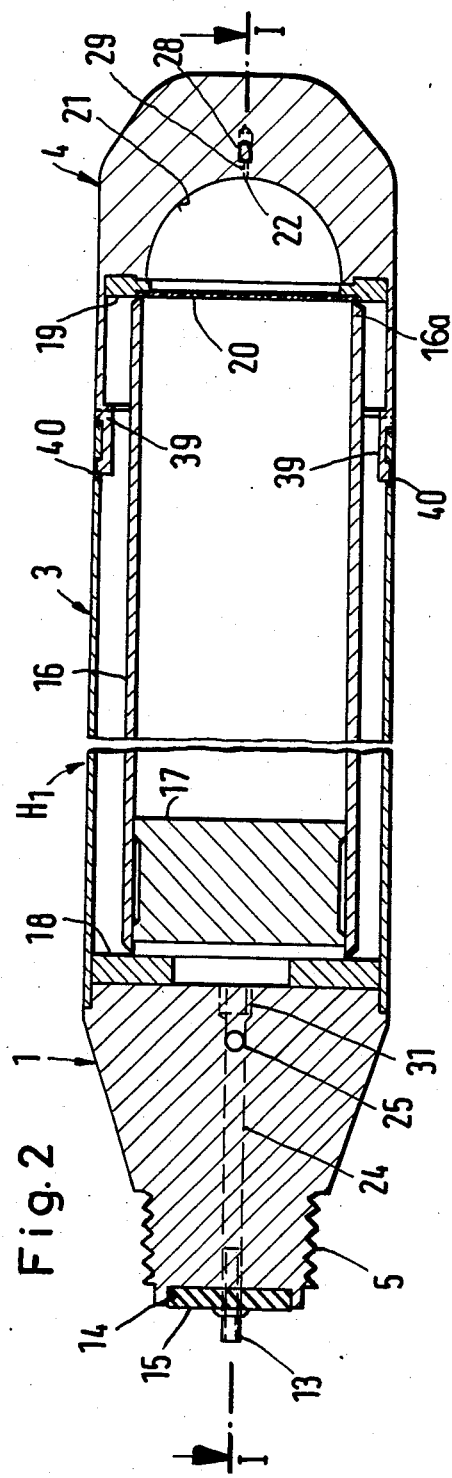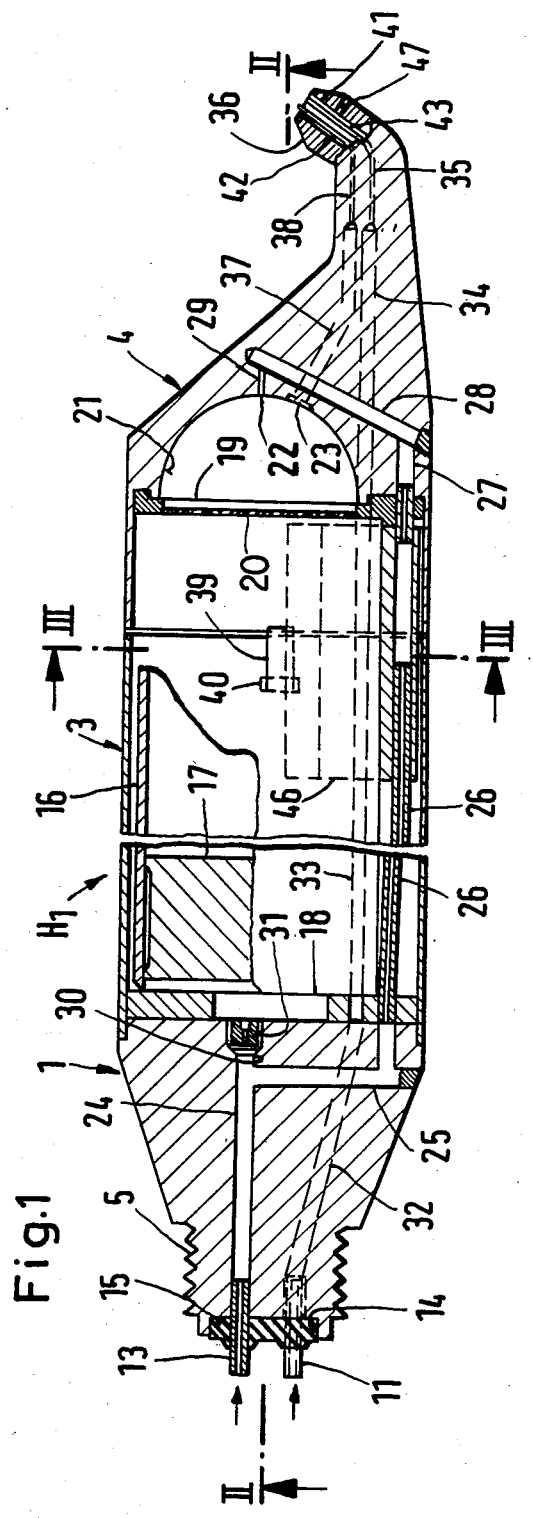

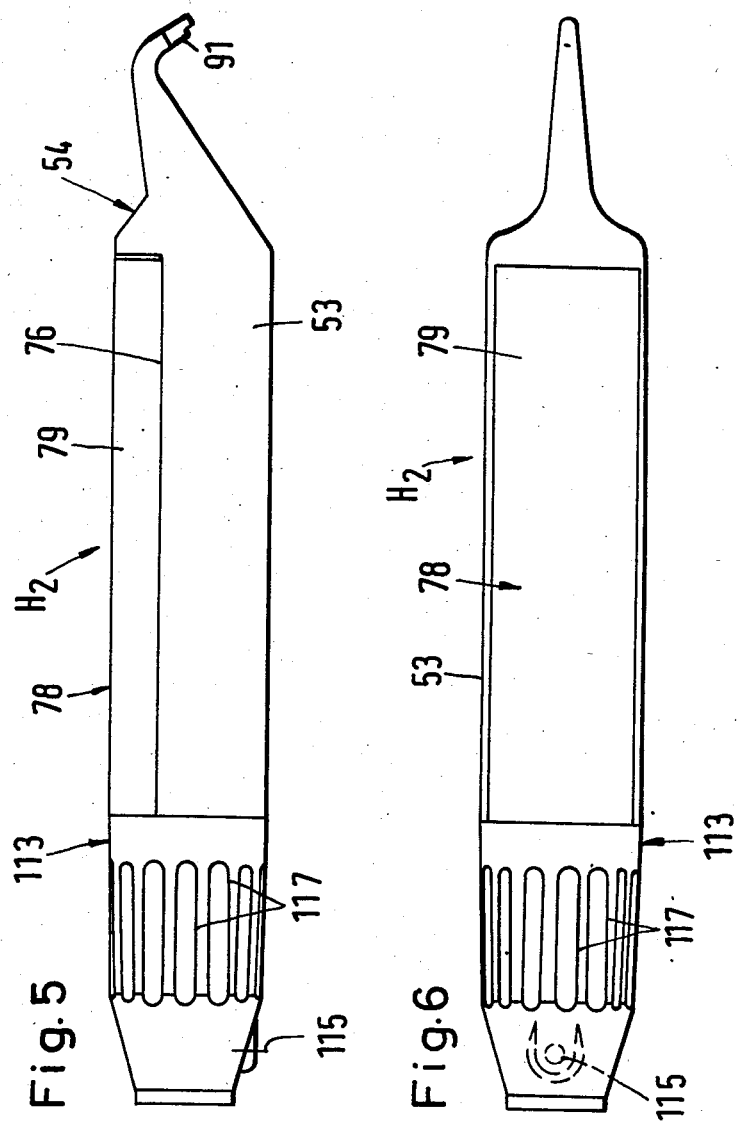

APPARATUS FOR REMOVING PLAQUE AND STAINS FROM THE SURFACES OF TEETH

BACKGROUND OF THE INVENTION

The present invention relates to oral hygiene appliances in general, and more particularly to improvements in apparatus for removing plaque and stains from the surfaces of teeth.

Conventional apparatus for removing plaque and stains from the surfaces of teeth have a nozzle which is manipulated by hand and has a first orifice serving to discharge a jet or stream containing a mixture of small (particularly pulverulent) solid particles and compressed air, and a second orifice which discharges a stream of water. Both streams are directed against the surface of the tooth whereby the jet or stream containing the mixture of solid particles and compressed air acts not unlike the jet which is discharged by the nozzle of a sand blasting machine. Conventional apparatus further comprise a stationary source of compressed air, a stationary supply of solid particles, and a stationary supply of pressurized water. Still further, the apparatus has a mixing chamber or vortex chamber wherein compressed air is intimately mixed with solid particles prior to entering the corresponding orifice of the nozzle, and means for connecting the nozzle with the two sources as well as with the supply of solid particles.

The vortex chamber is installed in a stationary housing for the supply of solid particles, and the corresponding connecting means includes a hose which connects the vortex chamber with the manually held nozzle. The discharge end of the hose has a coupling to allow for rapid attachment or detachment of the nozzle.

A drawback of the above outlined conventional apparatus is that the source of supply of solid material is stationary. This contributes to the bulk and cost of the apparatus. The particles of solid material contain salt and are likely to gather moisture on their way along the elongated path leading from the housing into the corresponding orifice of the nozzle. Moist particles tend to agglomerate in and to clog the hose, and particularly the nozzle. This necessitates frequent cleaning of the apparatus in order to reestablish the conditions for a predictable flow of the mixture toward and through the nozzle.

OBJECTS AND SUMMARY OF THE INVENTION

An object of the invention is to provide a novel and improved apparatus which can be used to remove plaque and stains from the surfaces of teeth and which is simpler, more compact and less expensive than heretofore known apparatus.

Another object of the invention is to provide the improved apparatus with novel and improved means for confining the supply of pulverulent solid material.

A further object of the invention is to provide an apparatus which is less likely to be clogged than conventional apparatus and which can stand long periods of continuous or intermittent use.

Still another object of the invention is to provide an apparatus which can supply an unchanging mixture of solid particles and a gaseous carrier medium for any desired interval of time.

An additional object of the invention is to provide the apparatus with a novel and improved handle and to construct and assemble the apparatus in such a way that it can receive a pressurized liquid medium and/or a compressed gaseous carrier medium from sources which are invariably available in a dentist's office, in a dental laboratory, in a hospital or in a similar institution.

Another object of the invention is to provide the improved apparatus with novel and improved means for admitting solid particles and the gaseous carrier medium into the vortex chamber.

The invention is embodied in an apparatus for removing plaque and stains from the surfaces of teeth with a jet containing a mixture of flowable solid particles and a gaseous medium. The apparatus comprises a hollow housing which constitutes a handle and includes a nozzle with at least one orifice serving to discharge the mixture against the teeth, and a receiving portion with an inlet which is connectable with a source of pressurized gaseous medium. The housing is formed with a vortex chamber which communicates with the inlet and with the orifice, and the apparatus further comprises a container for a supply of flowable solid particles. The container can constitute a cartridge which is removably installed directly in the housing and has an outlet for admission of flowable solid particles into the vortex chamber. The housing preferably further comprises a foraminous partition (for example, a sieve) which is interposed between the outlet of the container and the vortex chamber. The partition is preferably provided with openings whose dimensions match or only slightly exceed the dimensions of the solid particles in the container. The chamber is formed with an intake for compressed gaseous medium, and such intake is preferably located opposite the partition.

The apparatus preferably further comprises means for urging the supply of solid particles in the container into the outlet so that the supply of particles is always adjacent to one side of the partition. Such urging means preferably comprises a pneumatically operated piston which is movably installed in the container. The housing is then provided with a passage which conveys gaseous medium from the inlet to the piston, and such apparatus preferably further comprises flow restrictor means in the passage. The chamber is preferably provided in the nozzle.

The housing can be provided with means for conveying to the nozzle a stream of liquid medium which is sprayed onto the surfaces of teeth simultaneously with the spraying of the mixture. The nozzle is then provided with a second orifice for the stream of liquid medium, and such second orifice is preferably located rearwardly of the orifice for the mixture, as considered in the direction of flow of the jet from the nozzle. The nozzle is preferably configured in such a way that it discharges the jet in the form of a cone with an angle of divergence of less than 11 degrees.

The receiving portion of the housing is preferably designed to be connectable to the standard coupling element which supplies pressurized gaseous and liquid media to a dentist's drill. Such receiving portion has an additional inlet for pressurized liquid medium which is connectable to the coupling element simultaneously with the inlet for pressurized gaseous medium, and the apparatus preferably further comprises seals which are provided in the receiving portion and surround the inlets, at least when the receiving portion is connected to the coupling element.

The housing can include a tubular section and the container can constitute or include a cylinder which is removably received in the tubular section of the housing. Such apparatus preferably further comprises means for separably securing the nozzle to the tubular section, and the cylinder is insertable into and is removable from the tubular section when the section and the nozzle are separated from each other.

Alternatively, the housing can include a hollow section having a lateral aperture for insertion and removal of the container. The receiving portion is then reciprocable relative to the hollow section of the housing between a first position remote from the container and a second position of abutment with the container. Such apparatus further comprises means for releasably locking the receiving portion in the second position so that the receiving portion maintains the container in an optimum position. The container can include a cylinder having a first end portion which is provided with the aforementioned outlet and a second end portion which receives a part of the receiving portion in the second position of the receiving portion. Such part of the receiving portion is preferably rotatable relative to the cylinder in the hollow section of the housing, and the apparatus preferably further comprises the aforementioned foraminous partition which is interposed between the first end portion of the cylinder and the vortex chamber. The housing of the just described apparatus preferably further includes a sealing portion which surrounds the vortex chamber and partition and is in sealing engagement with the first end portion of the cylinder in the second position of the aforementioned part of the receiving portion. The piston of the urging means is preferably installed in the cylinder between the second end portion of the cylinder and the supply of solid particles in the container. The receiving portion is then formed with a passage which conveys pressurized gaseous medium from the respective inlet against the piston so that the piston urges the supply of solid particles toward and into the outlet of the container. The receiving portion of such apparatus is further provided with a second inlet for pressurized liquid medium and with first and second passages for reception of gaseous and liquid media from the respective inlets. The housing is then formed with a third passage connecting the first passage with the vortex chamber and with a fourth passage which connects the second passage with the orifice which is provided in the nozzle. The apparatus then further comprises a first fluidtight coupling between the first and third passages as well as a second fluidtight coupling which is installed between the second and fourth passages. At least one of the couplings preferably comprises a flexible conduit which permits rotation of the hollow section and the receiving portion of the housing relative to each other.

The just described apparatus preferably further comprises a bayonet mount which separably connects the receiving portion of the housing to the hollow section. To this end, the external surface of the receiving portion is formed with a helical groove and the hollow section has an internal surface which surrounds the external surface of the receiving portion and is provided with a projection or follower extending into the groove of the receiving portion. The groove includes a first portion having a pronounced positive lead and a second portion with a slightly negative lead, and the projection extends into the second portion of the groove when the receiving portion is properly connected to the hollow section of the housing.

The cross-sectional area of the orifice for the jet of a mixture of solid particles and gaseous medium can be constant all the way from the vortex chamber to the location where the jet issues from the nozzle.

The novel features which are considered as characteristic of the invention are set forth in particular in the appended claims. The improved apparatus itself, however, both as to its construction and its mode of operation, together with additional features and advantages thereof, will be best understood upon perusal of the following detailed description of certain specific embodiments with reference to the accompanying drawing.

BRIEF DESCRIPTION OF THE DRAWING

FIG. 1 is a somewhat schematic partly elevational and partly longitudinal sectional view of an apparatus which embodies one form of the present invention, the section being taken in the direction of arrows as seen from the line I—I of FIG. 2;

FIG. 2 is a sectional view as seen in the direction of arrows from the line II—II of FIG. 1;

FIG. 5 is an elevational view of a second apparatus;

FIG. 6 is a plan view of the apparatus which is shown in FIG. 5:

DESCRIPTION OF THE PREFERRED EMBODIMENTS

Figure 3:
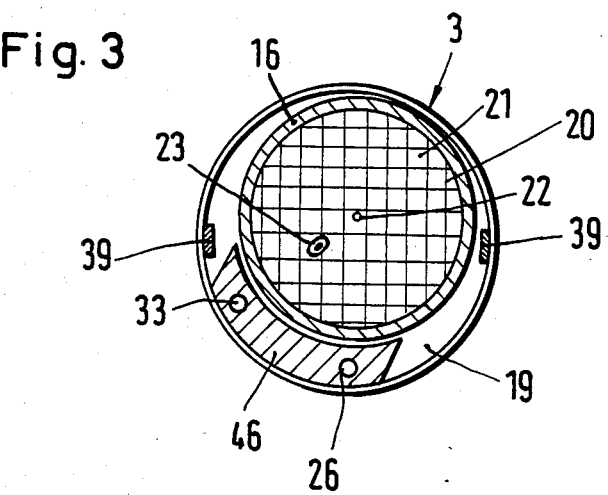
FIG. 3 is a transverse sectional view as seen in the direction of arrows from the line III—III of FIG. 1.
Figure 4:
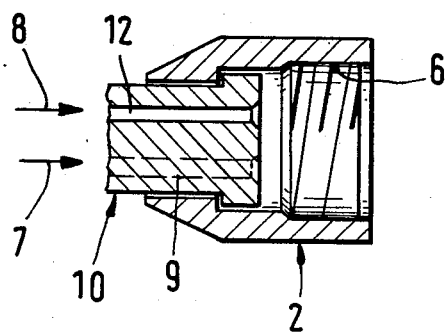
FIG. 4 is a fragmentary sectional view of an adapter which can supply compressed air and pressurized water to the apparatus of FIGS. 1 to 3.

Referring first to FIGS. 1 to 4, there is shown an oral hygiene appliance which constitutes an apparatus for removing plaque and stains (e.g., tobacco stains) from the surfaces of teeth. The apparatus comprises a hollow elongated housing H1 which constitutes a handle and includes a tubular central section 3, a nozzle 4 at one end of the section 3 and a receiving portion or section 1 at the other end of the section 3. The receiving portion 1 has external threads 5 which can mesh with the internal threads 6 of a standard coupling element or adapter 2 (FIG. 4) serving to connect the housing H1 with a source of compressed air (the source is indicated by the arrow 8) and with a source of pressurized liquid medium, particularly spray water (this source is denoted by the arrow 7). The adapter 2 can be used to connect the sources of pressurized liquid medium and compressed gaseous medium with a standard dentist's drill, i.e., such drill and the improved apparatus can be used interchangeably.

The receiving portion 1 of the housing H1 has a first inlet 11 which receives water from a first channel 9 in a conduit 10 forming part of the adapter 2, and a second inlet 13 which receives compressed air from a second channel 12 of the conduit 10. If the adapter 2 is connected to a drill, compressed air which is supplied via channel 12 is used to drive the rotary material removing, polishing or other tool of the drill. The inlets 11 and 13 are small tubes whose exposed portions extend into the discharge ends of the respective channels 9 and 12 when the receiving portion 1 is properly coupled with the adapter 2. One or more disc-shaped or otherwise configurated sealing elements 15 are provided in a recess 14 of the exposed end face of the receiving portion 1 and abut the adjacent face of the adapter 2 to prevent leakage of compressed air and/or pressurized water in the regions of the inlets 11 and 13. As can be seen in FIG. 1, the inlets 11 and 13 can extend through the illustrated disc-shaped sealing element 15 so that, when the latter is deformed in response to attachment of the receiving portion 1 to the adapter 2, it sealingly engages the inlets 11, 13 as well as the adjacent surfaces of the parts 1 and 2.

The improved apparatus further comprises a cylindrical container 16 for a supply of pulverulent or granular solid particles which are to be mixed with compressed air prior to being permitted to flow through a first orifice 42 of the nozzle 4 and to impinge upon the surfaces of teeth in the mouth of a patient or in the mouth of the person who is using the apparatus to clean her or his own teeth. The pulverulent or granular solid particles can constitute a salt, such as sodium bicarbonate, which can be used with advantage to remove plaque and/or stains from the surfaces of teeth. The container 16 can constitute a mass-produced cartridge which is discarded after the supply of solid particles therein is consumed, or a refillable cartridge which can be removed from the tubular section 3 of the housing H1 for the purpose of refilling and reinsertion into the section 3.

The means for urging the supply of solid material in a direction toward and into the open discharge end or outlet 16a of the container 16 comprises a piston or plunger 17 which is reciprocably mounted in and is in sealing engagement with the internal surface of the left-hand end portion of the container 16, as viewed in FIG. 1 or 2. The supply of solid particles (not specifically shown in FIGS. 1 and 2 but see the supply 80 in FIG. 7) is confined between the right-hand end face of the piston 17 and a foraminous partition 20 (preferably a sieve) which can be said to form part of the housing H1 and is preferably removably installed between the outlet 16a of the container 16 and the adjacent end of a substantially hemispherical mixing or vortex chamber 21 in the nozzle 4 of the housing H1.

The left-hand end face of the container 16, as viewed in FIGS. 1 and 2, abuts against the corresponding side of a ring-shaped sealing element 18 which is installed in the respective end portion of the tubular section 3 and abuts against the adjacent end face of the receiving portion 1. The central opening of the sealing element 18 defines a portion of the path along which a stream of compressed air can flow from the inlet 13 of the receiving portion 1 against that end face of the piston 17 which faces toward the inlets 11 and 13, i.e., away from the supply of solid particles in the container 16. A second ring-shaped sealing element 19 is recessed into the nozzle 4 and abuts against the adjacent end face of the container 16 (in the region of the outlet 16a) so as to prevent the escape of solid particles from the container in response to shifting of the piston 17 deeper into the interior of the container. The sealing element 19 operates between the outlet 16a of the container 16 and an internal shoulder of the nozzle 4. This sealing element further engages the marginal portion of the foraminous partition 20 which can be made of stainless steel or another suitable corrosion-resistant and wear-resistant material. The dimensions of openings in the partition 20 are preferably in the range of between 100 and 130 micrometers, and such dimensions preferably match or are only slightly greater than the dimensions of solid particles of the supply of such particles in the container 16. In other words, the cross-sectional areas of interstices in the sieve-like partition 20 preferably match or are only slightly greater than the cross-sectional areas of the solid particles between the partition and the piston 17. Such selection of dimensions of the openings in the partition 20 is desirable and advantageous because the dentist or another person who is in charge of using the improved apparatus need not be concerned with the orientation of the housing H1, i.e., solid particles cannot flow by gravity into the vortex chamber 21 of the nozzle 4 if the housing H1 is held in such position that the container 16 is disposed at a level above the chamber 21. Thus, in order to cause the solid particles to penetrate through the openings of the partition 20 and into the chamber 21, it is necessary to admit compressed air into the chamber 21 as well as to apply pressure against that side of the piston 17 which faces the inlets 11 and 13 of the receiving portion 1 so that the piston forces the solid particles of the column of such particles in the container 16 to penetrate through the partition 20 and into the chamber 21. This takes place only when the dentist has connected the inlets 11 and 13 with the sources of pressurized water and compressed air, respectively. Admission of solid particles into the vortex chamber 21 at an excessive rate could result in rapid clogging of the passage leading from the chamber 21 into the orifice 42 of the nozzle 4. Such passage includes an outlet 23 which receives a mixture of solid particles and compressed air from the chamber 21, a first channel 37 which receives the mixture from the outlet 23, and a second channel 38 (whose cross-sectional area is much smaller than that of the channel 37) which conveys the mixture from the channel 37 into the orifice 42. The channels 37, 38 and the outlet 23 are machined into or are otherwise formed in the nozzle 1.

The piston 17 is biased by compressed air which is supplied by the inlet 13 of the receiving portion 1 by way of a passage including a first channel 24 which communicates with the inlet 13 and a second channel 30 which communicates with the channel 24 and admits compressed air into the central opening of the sealing element 18. Such compressed air must flow through a flow restrictor 31 in the channel 30. The channels 24, 30 and the flow restrictor 31 are provided in the receiving portion 1 of the housing H1. The thus biased piston 17 ensures that the supply of solid particles in the container 16 is always adjacent to the outlet 16a and that the forward end of such supply bears against the corresponding side of the partition 20. Those solid particles which have penetrated into and beyond the openings of the partition 20 are entrained by the circulating compressed air which is admitted into the vortex chamber 21 by way of an inlet or intake 22. The latter is preferably provided in the nozzle 4 opposite the partition 20, e.g., substantially or exactly at the apex of the concave surface bounding the major portion of the vortex chamber 21. The provision of the piston 17, in conjunction with the partition 20, ensures that the apparatus can admit solid particles into the chamber 21 at an unchanging rate irrespective of whether the housing H1 is held in a substantially horizontal position or is oriented in such a way that the chamber 21 is located at a level above or below the partition.

An advantage of an inlet or intake 22 which is located exactly or substantially opposite the partition 20 is that the stream of compressed air which enters the chamber 21 flows substantially at right angles to the plane of the partition. Such stream penetrates through the partition 20 and loosens the solid particles forming the respective end of the column or supply of solid particles in the container 16. This ensures highly predictable penetration of solid particles into the chamber 21 and the formation of a mixture which contains an optimum percentage of solid particles in the gaseous carrier medium. Moreover, such guidance of compressed air on its way into the chamber 21 ensures a highly satisfactory mixing of solid particles with the gaseous carrier medium to thus reduce the likelihood of clogging the nozzle 4 and/or unsatisfactory cleaning action of the jet of the mixture which issues from the orifice 42.

The outlet 23 is preferably (but need not always be) located close to the inlet 22, i.e., opposite the central portion of the partition 20. The inlet 22 receives a stream of compressed air by way of a passage which is provided in part in the receiving portion 1 of the housing H1, in part in an insert 46 which is installed between the tubular section 3 and the container 16, and in part in the nozzle 4. This passage includes the aforementioned channel 24, a channel 25 which communicates with the channel 24, a channel 26 which is provided in the insert 46 and communicates with the channel 25, a channel 27 which is provided in the nozzle 4 and communicates with the channel 26, a channel 28 which communicates with the channel 27 and a channel 29 which connects the channel 28 with the inlet 22. The channel 26 can be replaced by the channel of a conduit (see FIG. 1) in the insert 46. The channel 29 constitutes a flow restrictor in that its cross-sectional area is only a small fraction of the cross-sectional area of the channel 28.

An advantage of the flow restrictor 31 in the channel 30 of the receiving portion 1 is that it ensures long-lasting retention of the piston 17 in contact with the respective end of the column of solid particles in the container 16 subsequent to an interruption of admission of compressed air into the channels 24 and 30 of the receiving portion 1. Moreover, the flow restrictor 31 ensures that the piston 17 continues to abut against the column of solid particles even if the housing H1 is held in a position such that the piston 17 is located at a level below the partition 20. Still further, the flow restrictor 31 ensures that the piston 17 remains in contact with the column of solid particles in the container 16 irrespective of the pressure in the vortex chamber 21. Consequently, the apparatus can proceed to discharge a jet of solid particles in a gaseous carrier medium in immediate response to renewed admission of compressed air into the inlet 13 because the piston 17 need not be shifted relative to the container 16 before it begins to urge the column of solid particles against the partition 20. Such mode of operation is highly desirable because the consistency of the jet which issues via orifice 42 of the nozzle 4 is predictable as soon as and whenever the apparatus is put to renewed use. The absence of any idle strokes of the piston 17 in response to admission of compressed air into the channel 24 is total or practically total if the interval of non-use of the improved apparatus is relatively short.

A second orifice 41 of the nozzle 4 receives a stream of pressurized water from the inlet 11 by way of a further passage including a channel 32 which is machined into or otherwise formed in the receiving portion 1 and communicates with the inlet 11, a channel 33 which is provided in the insert 46 and communicates with the channel 32 (the channel 33 can be defined by a pipe or conduit which is installed in the insert 46), a channel 34 provided in the nozzle 4 and communicating with the channel 33, and a flow restricting channel 35 which is also provided in the nozzle 4 and connects the channel 34 with the orifice 41. The orifices 41 and 42 are provided in a preferably detachable tip 36 of the nozzle 4.

The means for separably securing the nozzle 4 to the tubular section 3 of the housing H1 comprises several prongs 39 which are provided on the nozzle 4 and whose substantially hook-shaped or claw-shaped end portions are releasably held in complementary sockets 40 of the tubular section 3. The prongs 39 extend axially beyond a relatively thin tubular portion which forms part of the nozzle 4 and surrounds the sealing element 19 and the outlet 16a of the container 16.

The insert 46 has an arcuate shape and is installed in thetubular portion 3 of the housing H1 in a manner as shown in FIG. 3, i.e., so that the axis of the container 16 is parallel to (rather than coincident with) that of the tubular portion 3. The insert 46 urges the external surface of the container 16 into substantially linear contact with the internal surface of the tubular section 3.

When the apparatus is in use, the flow restrictor 31 admits compressed air against the adjacent side of the piston 17 so that the latter reliably maintains the column of solid particles in contact with the partition 20. At the same time, that part of the nozzle 4 which defines the channel 29 acts not unlike a small nozzle which injects a stream of compressed air into the vortex chamber 21 in a direction at right angles to the plane of the partition 20 to thus ensure predictable admission of solid particles into the chamber 21 through the openings of the partition 20 whereby the particles are mixed with the inflowing compressed air and are uniformly distributed therein prior to leaving the chamber 21 via outlet 23. As mentioned above, the jet of solid particles in the gaseous carrier medium which issues via orifice 42 acts not unlike the stream of solid particles issuing from a sand blasting nozzle and rapidly removes plaque and/or stains from the surfaces of teeth. The stream of compressed air which issues from the channel 29 via inlet 22 and flows at right angles to the plane of the partition 20 agitates and expels solid particles from the central portion of the respective end of the column and causes solid particles to penetrate through the partition 20 in the region of the sealing element 19 whereby such particles enter the chamber 21 and circulate therein until they find their way into the outlet 23 and thence into the orifice 42 of the nozzle 4. The streamlets of solid particles which flow along the concave surface bounding the chamber 21 in a direction from the sealing element 19 toward the outlet 23 are mixed with the stream of air entering via inlet 21 to undergo a further desirable mixing and homogenizing action prior to leaving the chamber 22 via outlet 23. The jet of solid particles in the gaseous carrier medium is accelerated during flow through the flow restricting channel 38 so that it acquires the required impact velocity not later than at the time it issues from the nozzle 4, namely a velocity which is necessary to ensure predictable and reliable removal of plaque and/or stains.

The piston 17 follows the advancement of the trailing end of the column of solid particles in the container 16 toward the outlet 16a to thus ensure that the conditions for removal or expulsion of solid particles from the container 16 into the vortex chamber 21 remain at least substantially unchanged irrespective of the length of the column of solid particles in the container. Such steady progress of the piston 17 in the container 16 reduces the likelihood of development of voids in the column of solid particles to thus even further reduce the likelihood of unpredictable admission of solid particles into the chamber 21.

The piston 17, in conjunction with the stream of compressed air which issues from the inlet 22 and penetrates through the central portion of the partition 20, contributes to proper orientation of normally elongated solid particles so that such particles can readily pass through the openings of the partition in regions which are adjacent to the sealing element 19. The aforediscussed dimensioning of openings in the partition 20 ensures that the solid particles cannot enter the chamber 21 by gravity flow so that the rate of their penetration through the partition 20 is not dependent upon the orientation of the housing H1, i.e., the rate of admission of solid particles into the chamber 21 is not dependent upon (it is neither assisted nor interfered with by) the force of gravity. This is desirable and advantageous because the dentist must frequently change the orientation of the housing H1 in order to reach the surfaces of teeth in the upper or lower jaw of the patient. Thus, the housing H1 can be held in a horizontal position, in an upright position in which the container 16 is located above or below the vortex chamber 21, or in an inclined position without affecting the rate of admission of solid particles into the chamber 21.

The flow restricting action of the throttle 31 is more pronounced than that of the flow restricting channel 29, and the flow restricting action of the channel 29 is more pronounced than that of the flow restricting channel 38. Such selection of throttling actions upon the piston 17, upon the stream of compressed air entering the vortex chamber 21, and upon the mixture flowing into the orifice 42 ensures that the piston 17 remains in adequate contact with the respective end of the column of solid particles in the container 16 for a reasonably long interval following an interruption of admission of compressed air into the channel 24 of the receiving portion 1. This is particularly desirable when the housing H1 is stored or supported in an upright position while the apparatus is not in use and while the piston 17 is located at a level below the partition 20. In the absence of the just discussed throttling actions at 31, 29 and 38, the piston 17 would be likely to rapidly descend in immediate response to or shortly after an interruption of admission of compressed air via inlet 13 so that the piston would have to perform a relatively short or a relatively long idle stroke (depending on the quantity of solid particles in the container 16) in response to immediate or delayed renewed admission of compressed air into the channel 24.

The orifice 41 preferably discharges a spray or stream of water simultaneously with the flow of a jet of solid particles in a gaseous carrier medium through and beyond the orifice 42 of the nozzle 4.

The orifices 41 and 42 are respectively defined by small-diameter pipes 43 which are installed in the tip 36 of the nozzle 4 and respectively receive water from the channel 35 and the mixture of solid particles and air from the channel 38. The pipe 43 which defines the orifice 42 extends forwardly beyond the other pipe 43, as considered in the direction of flow of the jet of solid particles and air from the nozzle 4, to thus ensure that water cannot penetrate into the discharge end of the pipe 43 for solid particles and thus cannot clog the path for the flow of the mixture in response to a resumption of utilization of the improved apparatus. The just discussed positioning of the pipes 43 relative to each other reduces the likelihood of malfunctioning of the apparatus upon resumption of its use because remnants of water which issue from the respective pipe 43 when the admission of water via inlet 11 is interrupted are much less likely to reach the discharge end of the path which is defined by the other pipe 43 for the flow of solid particles and compressed air toward the surface of a selected tooth. The pipes 43 are substantially parallel to each other, the same as the channels 35 and 38 in the nozzle 4. Any droplets of water which issue from the corresponding pipe 43 subsequent to an interruption of admission of water into the inlet 11 are likely to be retained by capillary action in the minute bore which is provided in the tip 36 of the nozzle 4 for the pipes 43. In order to further reduce the likelihood of penetration of water into the pipe 43 for the solid particles, the pipe 43 which defines the orifice 41 is formed with a small-diameter radial bore 47 which discharges remnants of water into the surrounding space when the admission of water via inlet 11 is interrupted. The bore 47 draws water from the orifice 41 due to a drop in pressure which develops around the tip 36 in the regions of the discharge ends of the pipes 43 when the apparatus is in actual use.

The angle of divergence of the jet of solid particles in the gaseous carrier medium should be less than 11 degrees, preferably not more than 10 degrees. This ensures that the entire jet can penetrate into the tooth spaces. The just described angle of divergence can be readily achieved if the (customary) size of solid particles is approximately 100 micrometers, if the length of the pipe 43 which defines the outlet 42 is at least between 5 and 12 mm, and if the inner diameter of such pipe is between 0.4 and 0.8 mm (preferably approximately 0.7 mm). A highly satisfactory angle of divergence is approximately 10 degrees for a pipe 43 having an inner diameter of approximately 0.7 mm and a length of 5-12 mm.

The user of the improved apparatus can gain access to the container 16 by the simple expedient of expelling the terminal portions of the prongs 39 from their sockets 40 and by pulling the nozzle 4 in a direction to the right, as viewed in FIG. 1 or 2.

The vortex chamber 21 can be provided in the container 16 in lieu of in the nozzle 4. The illustrated design is preferred at this time because the container 16 is less expensive; such container is preferably disposable after a single use.

The partition 20 can be made of a commercially available metallic sheet material of the type often used for sieves. Sieves with a mesh of between about 100 and 130 micrometers are standard articles. The feature that the partition need not be a specially manufactured article also contributes to lower cost of the apparatus.

In certain presently known apparatus for removal of plaque and stains from the surfaces of teeth, the nozzle is designed in such a way that the orifice for water surrounds the orifice which discharges solid particles in a gaseous carrier medium. Moreover, the discharge end of the orifice for the stream of water is coplanar with the discharge end of the other orifice. Therefore, when the admission of compressed air and pressurized water into the conventional apparatus is interrupted, remnants of water drip from the respective orifice toward the discharge end of the orifice for solid particles and the solid particles incrustate in the respective orifice to thus affect the rate of discharge of solid particles when the conventional apparatus is put to renewed use. Such problems can be avoided by the simple expedient of mounting the two pipes 43 in the tip 36 of the nozzle 4 in such a way that the discharge end of the pipe 43 which defines the orifice 42 extends forwardly and beyond the discharge end of the other pipe 43, as considered in the direction of flow of the jet of solid particles in the gaseous carrier medium.

The feature that the receiving portion 1 of the housing H1 can be sealingly coupled to a standard adapter 2 which is available in every dentist's office also contributes to lower cost of the improved apparatus. Thus, it is not necessary to provide an additional source of compressed air and/or an additional source of pressurized water because at least two prophylactic apparatus (including a conventional dentist's drill and the improved apparatus) can be attached to one and the same adapter.

Another important advantage of the improved apparatus is that the container 16 is installed in the housing H1. Thus, the housing, with the container therein, can be readily manipulated by a dentist or by another authorized person and the only connection between the apparatus and the stationary components is constituted by the conduit 10 which connects the adapter 2 to a stationary source of compressed air and with a stationary source of pressurized water. The weight of the container 16 adds only little to the overall weight of the apparatus, and such addition to the weight is more than balanced by the advantages and savings which are achieved by replacing a stationary source of solid particles with a container which has room in the housing. The container 16 is or can be placed into immediate proximity of the vortex chamber 21, i.e., the path for advancement of solid particles from the source of supply to the location where the particles are mixed with compressed air is short or such path need not be provided at all. This reduces the likelihood of incrustation of solid particles on their way from the container to the vortex chamber and obviates the need for frequent inspection and cleaning of the apparatus. Still further, prevention of incrustation of solid particles on their way from the source of supply into the vortex chamber reduces the likelihood of the formation of a non-homogeneous and fluctuating mixture of solid particles and gaseous carrier medium, regardless of whether the apparatus is used frequently and for longer intervals of time or less frequently and for short intervals.

Figure 10:
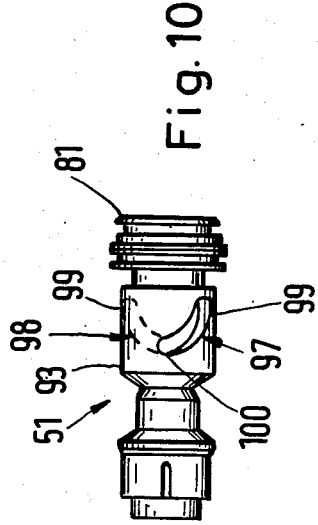
FIG. 10 is a smaller-scale elevational view of the receiving portion of the housing in the apparatus which is shown in FIGS. 5 to 9.
Figure 11:
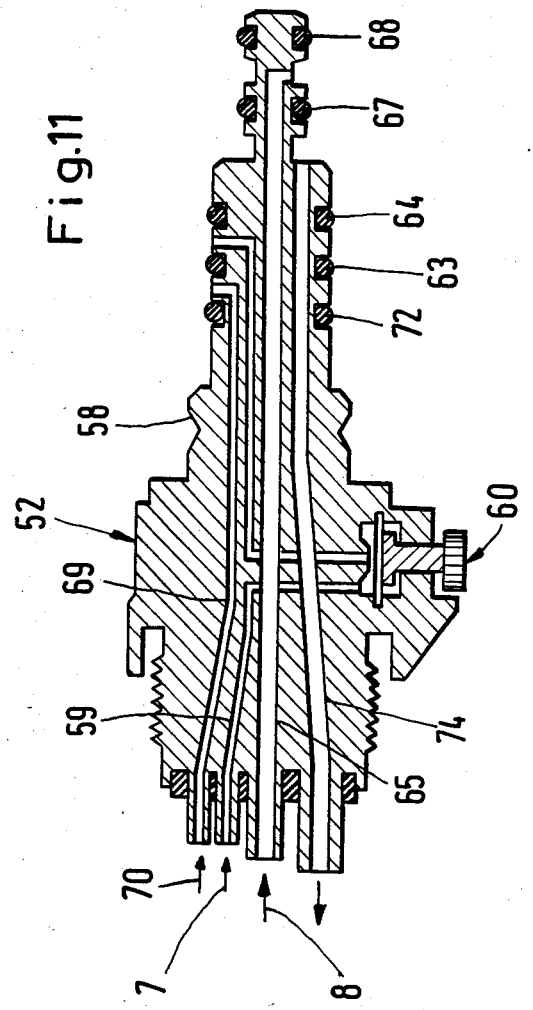
FIG. 11 is an axial sectional view of a standard adapter which can be used to supply compressed air and pressurized water to the apparatus of FIGS. 5 to 10.

FIGS. 5 through 11 show a modified apparatus whose housing or handle H2 has a receiving portion 51 (FIG. 10) which can be coupled to a conventional adapter 52 (FIG. 11). The latter is connected with a source (denoted in FIG. 11 by the arrow 7) of pressurized water and with a source (denoted in FIG. 11 by an arrow 8) of compressed air. When not used in conjunction with the improved apparatus, the adapter 52 can be used to supply pressurized water and compressed air to a conventional dentist's drill, not shown. The housing H2 further comprises a substantially centrally located substantially tubular hollow section 53 which is integral with or is more or less permanently connected to the nozzle 54.

Figure 7:
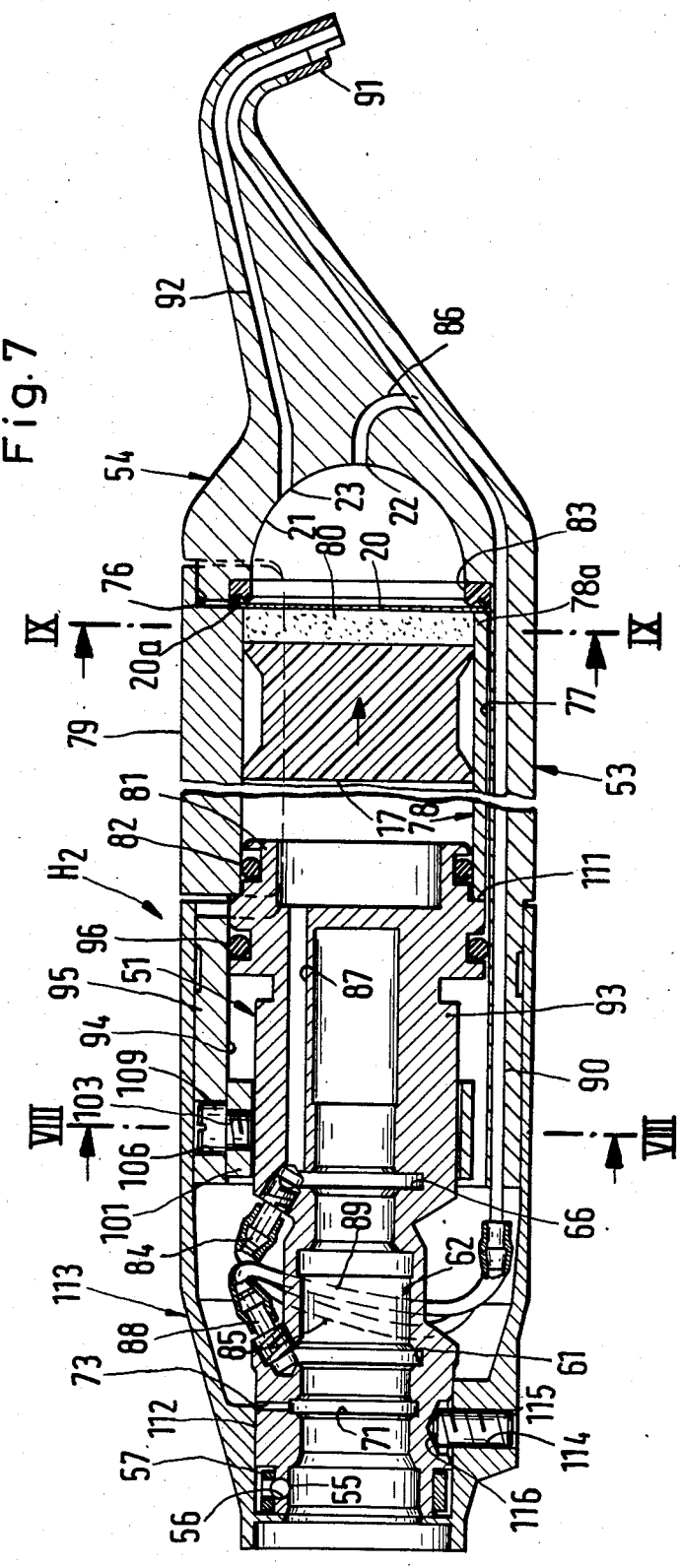
FIG. 7 is a longitudinal sectional view of the second apparatus, substantially as seen in the direction of arrows from the line VII—VII of FIG. 8.
Figure 9:
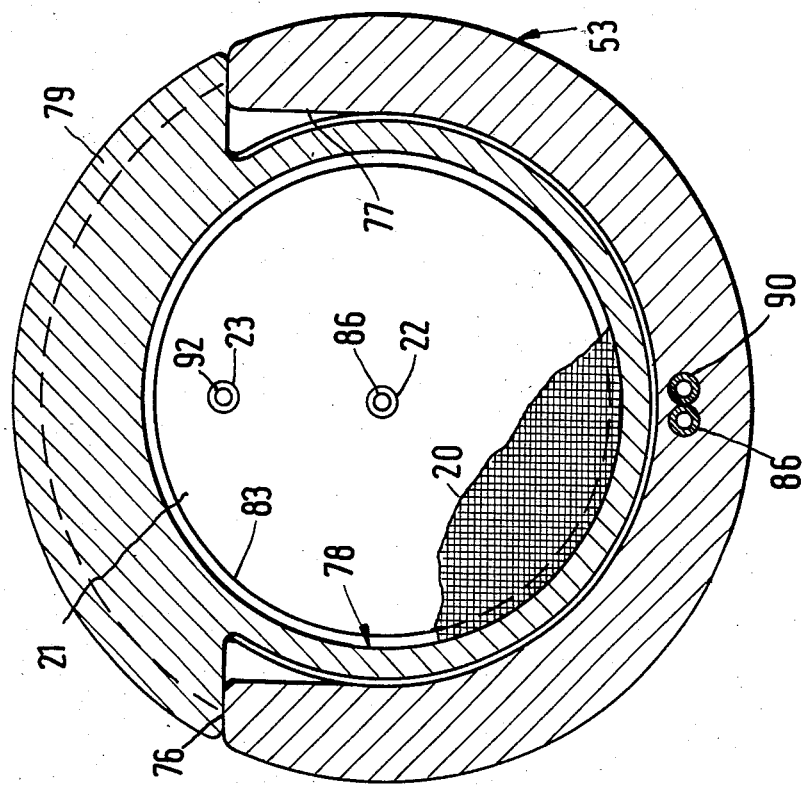
FIG. 9 is an enlarged sectional view as seen in the direction of arrows from the line IX—IX of FIG. 7.
Figure 8:
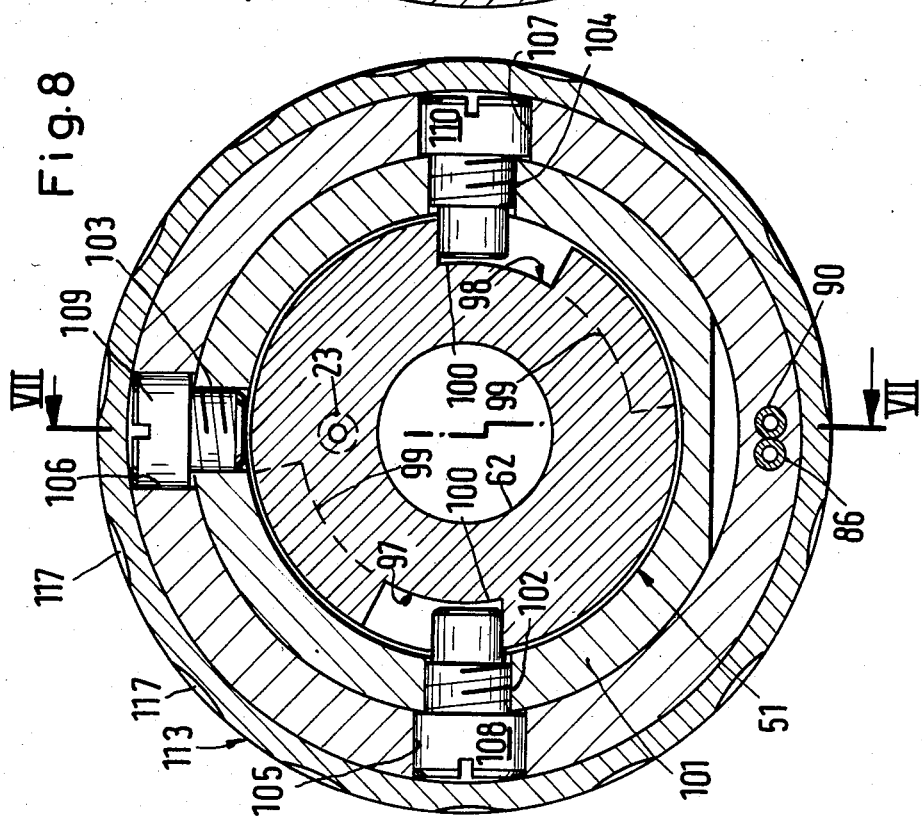
FIG. 8 is an enlarged transverse sectional view as seen in the direction of arrows from the line VIII—VIII of FIG. 7.

The manner in which the separable receiving portion 51 can be inserted into and rotated and reciprocated in the hollow section 53 of the housing H2 is shown in FIGS. 7 and 8. The receiving portion 51 contains a spherical male detent member 55 which is received in a radial bore 56 and is biased radially inwardly by a C-shaped spring 57. Only a portion of the detent member 55 can extend beyond the radially innermost portion of the bore 56. The spring 57 biases the inwardly extending portion of the detent member 55 into an external groove 58 of the adapter 52 when the latter is properly coupled with the corresponding end portion of the receiving portion 51.

The liquid medium (particularly spray water) which is supplied by the source 7 flows into a channel 59 of the adapter 52. The adapter 52 contains a manually adjustable valve 60 which controls the rate of water flow through the channel 59 and into an annular channel in the form of a circumferentially complete groove 61 (see FIG. 7) machined into the internal surface of the receiving portion 51. The groove 61 surrounds and communicates with a portion of an axial bore 62 in the receiving portion 51. When the adapter 52 is inserted into the bore 62, the groove 61 is flanked by two sealing rings 63 and 64 portions of which are recessed into complementary grooves in the external surface of the adapter.

When the adapter 52 of FIG. 11 is coupled to a drill, compressed air which is supplied by the source 8 serves to rotate the tool. When the adapter 52 is coupled with the receiving portion 51 of the housing H2, a channel 65 of the adapter supplies compressed air into an internal groove or channel 66 of the receiving portion 51 (see particularly FIG. 7) which is located inwardly of the groove 61 and is flanked by two sealing elements 67, 68 on the adjacent portion of the adapter 52.

The adapter 52 is formed with a further channel 69 which is connected with a source 70 of spray air and admits such air into a channel or groove 71 in the receiving portion 51. The groove 71 is flanked by the aforementioned sealing ring 63 and an additional sealing ring 72 of the adapter 52 when the latter is properly coupled to the receiving portion 51. The receiving portion 51 is formed with a radially outwardly extending bore 73 (see FIG. 7) which communicates with the groove 71 and permits spray air from the source 70 to escape. Such air is used only when the adapter 52 is coupled to a drill. A further channel 74 in the adapter 52 is used to establish a path for return flow of water from the mouth of a patient when the adapter is coupled to a drill. The left-hand end of the channel 74 (as viewed in FIG. 11) can be connected with a suction generating device, not shown.

The hollow portion 53 of the housing H2 has an elongated lateral aperture 76 (see FIG. 9) and defines a partly cylindrical compartment 77 for a substantially cylindrical container 78 storing a supply 80 of solid particles. The container 78 has an enlarged (substantially mushroom-shaped) portion 79 which closes the aperture 76 when the major part of the container 78 is properly received in the compartment 77.

The means for urging solid particles from the container 78 toward the partition 20 between the outlet 78a of the container and the mixing or vortex chamber 21 of the nozzle 54 again comprises a piston 17 which is reciprocable in the corresponding end portion of the container 78 and is biased forwardly (toward the partition 20) by compressed air which is supplied by the source 8. The peripheral surface of the piston 17 is in sealing engagement with but is slidable relative to the internal surface of the container 78 so that the piston prevents the escape of solid particles in a direction toward the receiving portion 51 of the housing H2. The foremost part 81 of the receiving portion 51 extends into the container 78 and carries a sealing ring 82 which is in sealing engagement with the internal surface at the left-hand end of the container 78, as viewed in FIG. 7. A further sealing ring 83 is provided at the front end of the container 78 (in the region of the outlet 78a) to prevent uncontrolled escape of solid particles into the nozzle 54.

The partition 20 can be made of stainless steel and can constitute a sieve with a mesh of between about 100 and 130 micrometers. The vortex chamber 21 is bounded in part by the flat right-hand side of the partition 20 and in part by a substantially hemispherical concave internal surface, of the nozzle 54, the same as in the embodiment of FIGS. 1 to 4.

The channel or groove 66 of the receiving portion 51 communicates with the inlet 22 of the chamber 21 by way of a nipple 84, a flexible hose 85 and a pipe 86 which is embedded in the hollow section 53. The latter is preferably made of a suitable synthetic thermoplastic material. The receiving portion 51 is further formed with a channel 87 which communicates with the channel or groove 66 and admits compressed air which is supplied by the source 8 against the exposed side of the piston 17 so that the latter is urged against the adjacent end of the column or supply 80 of solid particles in the container 78. That end portion of the channel 87 which is defined by the foremost part 87 of the receiving portion 51 is greatly enlarged, and the smaller-diameter part of the channel 81 constitutes a flow restrictor.

The channel or groove 61 of the receiving portion 51 communicates with the interior of a nipple 88 which extends radially outwardly beyond the receiving portion and is connected with a flexible hose 89 serving to admit pressurized water to a pipe 90 which extends through the hollow section 53 and all the way into the tip 91 of the nozzle 54.

The outlet 23 of the vortex chamber 21 admits the mixture of solid particles and gaseous carrier medium into a conduit 92 which is installed in the nozzle 54 and discharges the mixture slightly ahead of the locus of discharge of pressurized water in the tip 91. The inner diameter of the conduit 92 is constant all the way from the outlet 23 of the chamber 21 to the locus of discharge of the mixture from the conduit 92.

An intermediate part 93 of the receiving portion 51 (beyond the foremost part 81) is received in an axial bore or hole 94 of the corresponding part 95 of the hollow section 53, and the parts 93, 95 cooperate to deform a sealing ring 96 and to thus prevent leakage of compressed air which is admitted by the channel 87.

As can be seen in FIGS. 8 and 10, the external surface of the part 93 of the receiving portion 51 is formed with two guide grooves 97 and 98 which are disposed diametrically opposite each other. Each of these grooves resembles a portion of a helix and extends along an arc of approximately 90 degrees, as considered in the circumferential direction of the receiving portion 51. Each of the guide grooves 97, 98 has a relatively long first portion 99 with a pronounced positive lead and a relatively short second portion 100 with a slight negative lead. The longer portion 99 of each guide groove is nearer to the foremost part 81 of the receiving portion 51 than the respective shorter portion 100.

FIGS. 7 and 8 show that the bore or hole 94 in the part 95 of the hollow section 53 contains a ring 101 which is formed with radially extending tapped through holes 102, 103 and 104. The holes 102 and 104 are located diametrically opposite each other. The holes 102, 103, 104 register with somewhat larger radial holes 105, 106 and 107 in the part 95. The holes 102, 103, 104 receive the threaded shanks of bolts 108, 109, 110 whose heads are received in the respective holes 105, 106, 107. The tips of the shanks of bolts 108 and 110 respectively extend into the guide grooves 97 and 98. The shank of the bolt 109 is shorter so that it terminates radially outwardly of the part 93 of the receiving portion 51. That portion of the part 93 which defines the grooves 97, 98 and the bolts 108, 110 together constitute a bayonet mount between the receiving portion 51 and the tubular section 53, and the bolt 109 serves to hold the ring 101 against axial movement in the hole or bore 94.

The shanks of the bolts 108, 110 extend into the first portions 99 of the respective grooves 97, 98 before the foremost part 81 of the receiving portion 51 (which is rotatable and axially movable in the bore 94 of the tubular section 53) enters the container 78. If the receiving portion 51 is thereupon rotated, it is caused to move in a direction to the right, as viewed in FIG. 7, because the shanks of the bolts 108, 110 constitute followers which track the respective helical grooves 97 and 98. This causes the foremost part 81 of the receiving portion 51 to penetrate into the container 78. Such penetration is terminated when an annular shoulder 111 of the receiving portion 51 reaches and sealingly engages the adjacent end face of the container 78. The container 78 is then urged forwardly toward the vortex chamber 21. This, in turn, causes the frame-like marginal sealing portion 20a of the partition 20 to bear against the sealing ring 83. At such time, the tips of the shanks of bolts 108, 110 extend into the second portions 100 of the respective guide grooves 97 and 98. The material surrounding the second portions 100 of the grooves 97, 98 can be said to constitute a means for releasably locking the receiving portion 51 to the hollow section 53 of the housing H2 due to the negative lead of second portions 100. If the operator wishes to separate the portion 51 from the section 53, the portion 51 is turned in the opposite direction through an angle of approximately 90 degrees whereupon the portion 51 can be extracted from the section 53, at least to the extent which is necessary to withdraw the substantially cylindrical portion of the container 78 from the compartment 77 of the section 53.

The rearmost part 112 of the receiving portion 51 extends from the part 95 of the hollow section 53 and is surrounded by a cap screw 113 which is rotatably mounted on the part 95. The cap screw 113 has a radially extended tapped bore 114 which receives a threaded pin 115 in such a way that the tip of the pin 115 extends into a radially extending bore 116 in the external surface of the rearmost part 112 of the receiving portion 53. This ensures that the cap screw 113 is held against angular and/or radial movements relative to the receiving portion 51, i.e., the latter can be rotated in response to rotation of the cap screw 113. The external surface of the cap screw 113 is preferably formed with axially parallel flats, flutes or like configurations 117 which facilitate its rotation relative to the tubular section 53.

The mode of operation of the apparatus which embodies the structure of FIGS. 5 to 11 is substantially identical with that of the apparatus which is shown in FIGS. 1 to 4.

In the apparatus of FIGS. 5 to 11, the container 78 is insertable and removable by moving it laterally of the hollow section 53, and the receiving portion 51 performs the additional function of releasably holding the inserted container 78 in an optimum position with reference to the partition 20 and vortex chamber 21. Thus, the nozzle 54 can be made integral with the tubular section 53 and the housing H2 need not be dismantled in order to allow for extraction or insertion of the container 78.

The parts 84, 85 constitute a first fluidtight coupling which establishes communication between the passage including the groove 66 and the passage including the pipe 86, and the parts 88, 89 constitute a second fluidtight coupling which allows for communication between the passage including the channel or groove 61 and the passage that is defined by the pipe 90. Each of the two couplings allows for limited angular and axial movements of the receiving portion 51 and hollow section 53 relative to each other so that the operator can engage or disengage the aforediscussed bayonet mount. The foremost part 81 of the receiving portion 51 not only seals the rear end of the container 78 but also holds the container in an optimum position, as considered radially of the hollow section 53.

The pipe 92 (whose inner diameter is constant all the way from the outlet 23 of the vortex chamber 21 to the locus of discharge of the mixture of solid particles and compressed air) exhibits the advantage that its interior is less likely to be clogged than if the passage between the vortex chamber and the corresponding orifice of the nozzle 54 were to contain one or more flow restrictors. Moreover, the interior of the pipe 92 can be readily and rapidly cleaned.

Without further analysis, the foregoing will so fully reveal the gist of the present invention that others can, by applying current knowledge, readily adapt it for various applications without omitting features that, from the standpoint of prior art, fairly constitute essential characteristics of the generic and specific aspects of our contribution to the art and, therefore, such adaptations should and are intended to be comprehended within the meaning and range of equivalence of the appended claims.

We claim:

1. Apparatus for removing plaque and stains from the surfaces of teeth with a jet containing a mixture of flowable solid particles and a gaseous medium, comprising a hollow housing constituting a handle and including a nozzle having at least one orifice arranged to discharge the mixtures against the teeth, and a receiving portion having an inlet connectable with a source of pressurized gaseous medium, said housing having a vortex chamber in communication with said inlet and said orifice; and a container for a supply of flowable solid particles in said housing, said container having outlet means for addision of flowable solid particles into said chamber, and said housing further including a foraminous partition which is interposed between the outlet means of said container and said chamber.

2. The apparatus of claim 1 for removing plaque and stains with a jet containing solid particles having predetermined dimensions, wherein said partition has openings whose dimensions match or only slightly exceed said predetermined dimensions.

3. The apparatus of claim 1, wherein said chamber has an intake for compressed gaseous medium, said intake being located opposite said partition.

4. The apparatus of claim 1, further comprising means for urging the supply of solid particles in said container into said outlet means.

5. The apparatus of claim 4, wherein said urging means comprises a pneumatically operated piston which is movably installed in said container.

6. The apparatus of claim 5, wherein said housing has a passage for conveying gaseous medium from said inlet to said piston and flow restrictor means in said passage.

7. The apparatus of claim 1, wherein said partition includes a sieve.

8. The apparatus of claim 1, wherein said chamber is provided in said nozzle.

9. The apparatus of claim 1, wherein said orifice has a diameter between 0.4 and 0.8 mm, preferably 0.7 mm, and a length of between 5 and b 12 mm.

10. The apparatus of claim 1, wherein said housing has means for conveying to said nozzle a stream of liquid for spraying onto the surfaces of teeth simultaneously with spraying of said mixture.

11. The apparatus of claim 10, wherein said nozzle has a second orifice for the stream of liquid and said second orifice is located rearwardly of the orifice for said mixture, as considered in the direction of flow of the jet from the respective orifice.

12. The apparatus of claim 11, wherein said nozzle has means for discharging, by way of the respective orifice, said mixture in the form of a cone-shaped jet with an angle of divergence less than 11 degrees.

13. The apparatus of claim 1 for attachment of said receiving portion to the standard coupling element which supplies pressurized gaseous and liquid media to a dentist's drill, wherein said receiving portion has an inlet for pressurized liquid medium which is connectable to the coupling element simultaneously with the inlet for pressurized gaseous medium and further comprising a sealing element provided in said receiving portion and surrounding said inlets at least when said receiving portion is connected with the coupling element.

14. The apparatus of claim 1, wherein said housing includes a tubular section and said container includes a cylinder which is removably received in said section.

15. The apparatus of claim 14, further comprising means for separably securing said nozzle to said tubular section, said cylinder being insertable into and removable from said section when said section and said nozzle are separated from each other.

16. The apparatus of claim 1, wherein said housing further includes a hollow section having a lateral aperture for insertion and removal of said container.

17. The apparatus of claim 16, wherein said receiving portion is reciprocable relative to said section between a first position remote from and a second position of abutment with the container therein; and further comprising means for releasably locking said receiving portion in said second position.

18. The apparatus of claim 18, wherein said container includes a cylinder having a first end portion provided with said outlet means and a second end portion receiving a part of said receiving portion in the second position of the latter.

19. The apparatus of claim 19, wherein said part of said receiving portion is rotatable relative to the cylinder in said section.

20. The apparatus of claim 19, wherein said housing includes a sealing portion surrounding said chamber and said partition and being in sealing engagement with the first end portion of said cylinder in the second position of said part of said receiving portion.

21. The apparatus of claim 18, further comprising a piston installed in said cylinder between said second end portion and the supply of solid particles in said container, said receiving portion having a passage for conveying pressurized gaseous medium from said inlet against said piston so that the latter urges the supply of solid particles toward and into said outlet means.

22. The apparatus of claim 17, wherein said receiving portion has a second inlet for pressurized liquid medium and first and second passages for reception of gaseous and liquid media from the respective inlets, said housing having a third passage connecting said first passage with said chamber and a fourth passage connecting said second passage with the orifice which is provided in said nozzle for a stream of liquid medium; and further comprising a first fluidtight coupling between said first and third passages and a second fluidtight coupling between said second and fourth passages.

23. The apparatus of claim 22, wherein at least one of said couplings comprises a flexible conduit which permits rotation of said section and said receiving portion relative to each other.

24. The apparatus of claim 17, further comprising a bayonet mount separably connecting said receiving portion to said section.

25. The apparatus of claim 24, wherein said receiving portion has an external surface and said section has an internal surface surrounding said external surface, said bayonet mount having a helical groove in said external surface and a projection extending beyond said internal surface and into said groove, said groove having first and second portions with different leads including a positive lead in said first portion and a negative lead in said second portion, said projection extending into the second portion of said groove when said receiving portion is connected to said section.

26. The apparatus of claim 1, wherein the cross-sectional area of said orifice is constant all the way from said chamber to the location where the jet issues from said nozzle.

* * * * *